United States Patent [19]

Magid et al.

[11] Patent Number: 4,640,642

[45] Date of Patent: Feb. 3, 1987

[54] BENDABLE ELBOW CONNECTOR

[75] Inventors: Robert Magid, 188 Goldhurst Terrace, West Hampstead, London NW6, England; John Choong, London, England

[73] Assignee: Robert Magid, London, England

[21] Appl. No.: 693,666

[22] Filed: Jan. 22, 1985

[30] Foreign Application Priority Data

Jan. 27, 1984 [GB] United Kingdom ............... 8402150

[51] Int. Cl.$^4$ ............................................. F16C 11/06
[52] U.S. Cl. .................................... 403/157; 403/161; 16/386
[58] Field of Search ............... 403/157, 161, 162, 150, 403/151; 474/214, 215, 216, 217; 16/386

[56] References Cited

U.S. PATENT DOCUMENTS 84,772 12/1868 Shannon ................................. 16/386

FOREIGN PATENT DOCUMENTS 821448 11/1951 Fed. Rep. of Germany ...... 403/157
410673 8/1976 U.S.S.R. ............................... 403/157

*Primary Examiner*—Andrew V. Kundrat
*Attorney, Agent, or Firm*—Christie, Parker & Hale

[57] ABSTRACT

The connector comprises a first element having one end provided with a single first eye, a second element having one end provided with two coaxial second eyes axially spaced to receive between them the single eye, and a pivot pin insertable through all the three eyes, when the latter are coaxially aligned, to thereby join the two elements together. The pivot pin consists of two parts insertable through the eyes. Each part has a first end provided with a first engagement means and an opposite second end provided with a resilient second engagement means, and each second eye has at its axially outer side a third engagement means, whereby on full insertion of the parts through the eyes the parts and the second eyes are interlocked by the engagement means.

9 Claims, 7 Drawing Figures

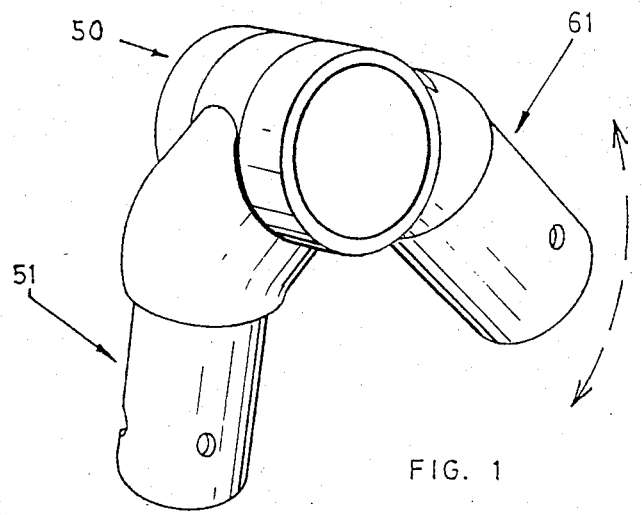
FIG. 1
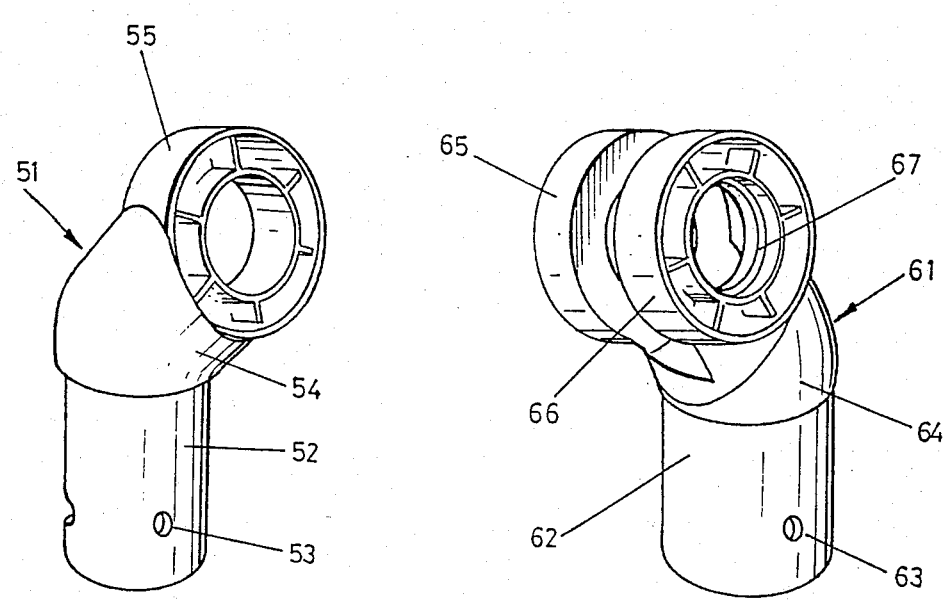
FIG. 2
FIG. 3

BENDABLE ELBOW CONNECTOR

The invention relates to a bendable elbow connector which has a wide application, but is particularly suitable for use with a dismountable structure disclosed in my co-pending U.S. patent application Ser. No. 604,905.

The aim of the invention is to devise a bendable elbow connector which can be easily assembled and comprises two arms which can be quickly, simply, safely and permanently interconnected in a manner allowing their angular movement (bending) relative to each other.

This is achieved according to the invention by the bendable elbow connector claimed in claim 1.

The invention will now be described, by way of example, with reference to the accompanying diagrammatic drawings, in which:

FIG. 1 shows a bendable elbow connector;

FIGS. 2 and 3 show, respectively, the two arms of the connector shown in FIG. 1;

Figure 4:
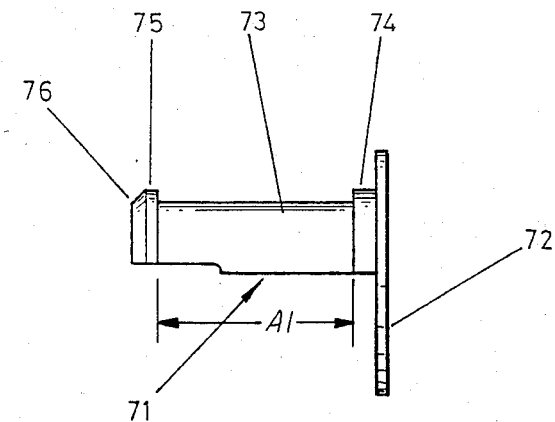
FIG. 4 shows a pin half.
Figure 5:
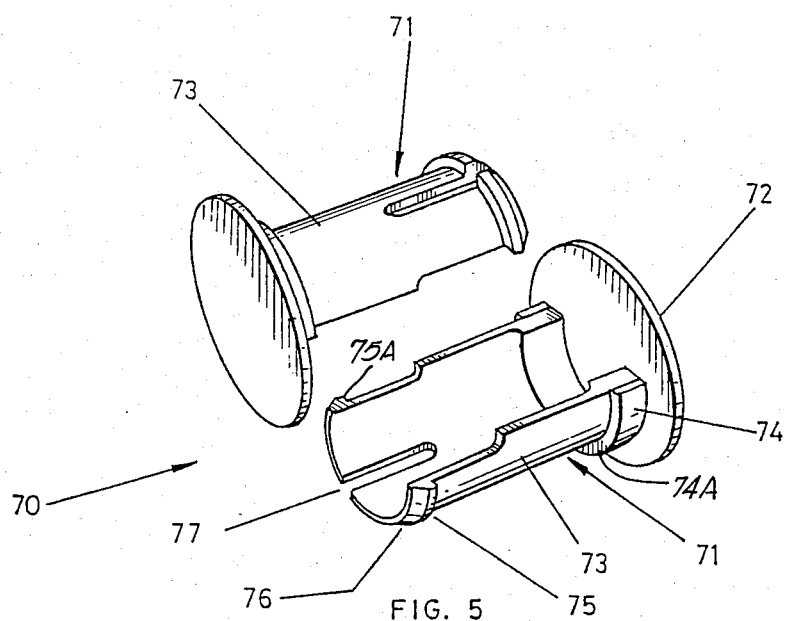
FIG. 5 shows a pivot pin composed or two pin halves shown in FIG. 4.
Figure 6:
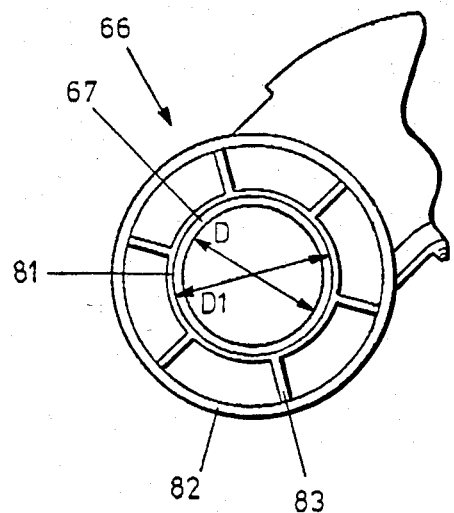
FIG. 6 is a front elevation of a part of the arm illustrated in FIG. 3.
Figure 7:
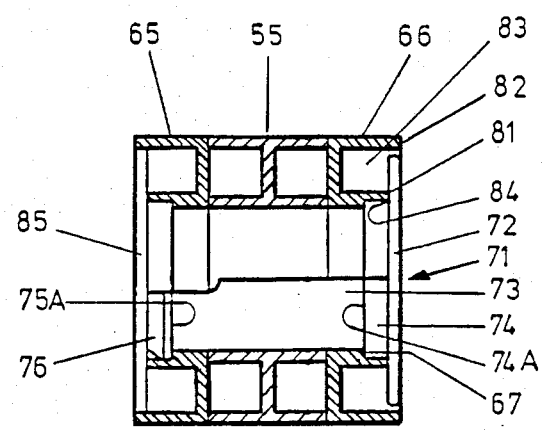
FIG. 7 is an axial section through the three eyes of the connector interconnected by the pivot pin.

The drawings illustrate a bendable elbow connector 50 comprising two arms 51 and 61 interconnected by a joint of the type known as knuckle joint.

The arm 51 comprises an attachment member 52 which is at one end connected to a core 54 the face of which, adjacent the member 52, defines a shoulder. On its side remote from the member 52 the core 54 carries a centrally positioned eye 55.

The arm 61 comprises an attachment member 62 connected at one end to a core 64 the face of which, adjacent the member 62, defines a shoulder. The opposite end of the core 64 carries two axially spaced-apart parallel and coaxial eyes 65, 66. The eyes 55, 65, 66 have the same inner diameter D. Each of the eyes 65, 66 has at its axially outer side an inner annular recess 84 of an inner diameter $D_1 > D$ defining a radially extending annular inner flange having a radial outer face 67. The two outer faces 67 are spaced apart by a distance A not shown. In the illustrated embodiment each of the eyes 55, 65, 66 is made up of an inner tubular element or hub 81 and outer tubular element or rim, 82 the hub 81 and rim being coaxially united by spokes 83. The hub 81 and spokes 83 of the eyes 65, 66 are on the axially outer side shorter than the rim whereby a circular space is defined. Naturally, the eyes could be solid and the circular space could be in the form of a recess.

For assembly, the eye 55 of the arm 51 is inserted between the eyes 65, 66 of the arm 61 such that it is coaxial therewith and secured in position by a pivot pin 70, consisting of two identical pin halves 71 inserted from opposite sides to extend through all the three eyes 55, 65, 66, whereby pivotal connection of the arms 51 and 61 is obtained.

Each pin half 71 comprises a flange 72 in the shape of a circular disk to the central region of which is coaxially firmly connected a trough-shaped, substantially semi-cylindrical shell 73 of an outer diameter are slightly smaller than D. The shell 73 has at its end adjacent the flange 72 a first outer shoulder 74 which is substantially semi-annular and rectangular in axial section and has a radial axially inner face 74A. A portion of the opposite end of the shell 73 is reduced in size to be slightly less than semi-cylindrical and carries a second outer shoulder 75 which is part-annular and has a slanted, substantially part-frusto-conical axially outer face 76 and a radial axially inner face 75A. The two inner faces 74A, 75A are spaced apart by a distance $A_1$, which is slightly greater than the distance A between the outer faces 67. The shoulders 74 and 75 have an outer diameter slightly smaller than $D_1$. An axial slit 77 passes through the middle of the reduced end portion of the shell 73 and shoulder 75 and divides them into two mirror-symmetrical end-pieces.

Each pin half 71 is made of a resilient material so that, when the pin half 71 is pushed by an axial force through the eyes 55, 65, 66, the radial components of said axial force acting on the shoulder 75 deflect its end-pieces radially inwardly allowing the shoulder 75 to pass through the coaxially aligned eyes, and on reaching the annular recess to return to its original position. The slanted outer face 76 facilitates insertion of the pin half 71 through the eyes 55, 65, 66. When the pin half 71 is fully inserted the inner flanges of the eyes 65, 66 are situated between its shoulders 74 and 75, thus preventing the pin half 71 from being withdrawn therefrom because in that position the inner faces of the shoulders 74, 75 engage with the adjacent outer faces 67 of the eyes 65, 66. In the fully inserted position the flange 72 is received in said circular space and is radially outwardly surrounded by said rim.

In the illustrated embodiment the attachment member 52 is formed by a male socket provided with four holes 53 and the attachment member 62 is formed by a female socket provided with two holes 63 described in detail in the above mentioned co-pending patent application. Alternatively, both the arms 51, 61 can be formed by or comprise the same sockets, either male or female. Naturally, another suitable structural element may be used instead of the sockets, e.g. a sleeve or a solid bar of a suitable shape and size, which may be provided with means, e.g. a thread, for the connection of the arm to another element.

In the illustrated embodiment the connector is wholly made of a plastics material, but may be made from another material, e.g. metal.

We claim:

1. A bendable elbow connector comprising a first element having one end provided with a single first eye, a second element having one end provided with two coaxial second eyes axially spaced to receive between them said single eye, and a pivot pin insertable through all said three eyes, when the latter are coaxially aligned, to thereby join said two elements together, wherein said pivot pin consists of two parts insertable through said eyes, each said part having a first end provided with a first engagement means and an opposite second end provided with a resilient second engagement means, and each said second eye having at its axially outer side a third engagement means, whereby on full insertion of said parts through said eyes said parts at each end and said second eyes are interlocked by said engagement means.

2. A connector according to claim 1, wherein each said pin part is formed by a trough-shaped, partly substantially semi-cylindrical shell which carries at its first end said first engagement means in the form of a first outer shoulder and its second end is reduced in size to be less than semi-cylindrical and carries said second engagement means in the form of a second outer shoulder.

3. A connector according to claim 2, wherein an axial slit passes through the middle of at least a part of said second end and through said second outer shoulder.

4. A connector according to claim 3, wherein said first outer shoulder has a radial axially inner face, and said second outer shoulder has a radially axially inner face, and each of said third engagement means has a radial axially outer face, the axial distance between said axially inner faces being slightly greater than the axial distance between said axially outer faces.

5. A connector according to claim 2, wherein said second outer shoulder has a slanting axially outer face.

6. A connector according to claim 2, wherein the semi-cylindrical shell carries axially outwardly of said first outer shoulder a substantially circular flange.

7. A connector according to claim 1, wherein at least one of the eyes comprises a hub and a rim interconnected by spokes.

8. A connector according to claim 1, wherein said elements are arms.

9. A connector according to claim 1, wherein on full insertion of said parts through said eyes said parts and said second eyes are so interlocked that said parts cannot be removed without damage to the connector.

* * * * *